United States Patent
Mullin

(10) Patent No.: US 11,737,887 B2
(45) Date of Patent: *Aug. 29, 2023

(54) SPINAL IMPLANT

(71) Applicant: Brad Mullin, New Albany, OH (US)

(72) Inventor: Brad Mullin, New Albany, OH (US)

(*) Notice: Subject to any disclaimer, the term of this patent is extended or adjusted under 35 U.S.C. 154(b) by 260 days.

This patent is subject to a terminal disclaimer.

(21) Appl. No.: 17/114,791

(22) Filed: Dec. 8, 2020

(65) Prior Publication Data

US 2021/0085484 A1 Mar. 25, 2021

Related U.S. Application Data

(63) Continuation of application No. 16/450,274, filed on Jun. 24, 2019, now Pat. No. 10,881,525, which is a
(Continued)

(51) Int. Cl.
*A61F 2/44* (2006.01)
*A61B 17/70* (2006.01)
(Continued)

(52) U.S. Cl.
CPC ............ *A61F 2/4455* (2013.01); *A61B 17/70* (2013.01); *A61B 17/7002* (2013.01);
(Continued)

(58) Field of Classification Search
CPC .. A61F 2/44; A61F 2/4455; A61F 2/28; A61F 2/2846; A61F 2/4405; A61B 17/70;
(Continued)

(56) References Cited

U.S. PATENT DOCUMENTS 5,591,235 A 1/1997 Kuslich
8,328,848 B2 12/2012 Lowery et al.
(Continued)

FOREIGN PATENT DOCUMENTS

CN 2875347 Y 3/2007
CN 101564317 B 7/2012
(Continued)

OTHER PUBLICATIONS

Extended European Search Report dated Jun. 8, 2021; Application 18864910.7-1132/ 3691553 PCT/US2018/054349; 9 pages.
(Continued)

*Primary Examiner* — Christopher J Beccia
(74) *Attorney, Agent, or Firm* — Vorys, Sater, Seymour and Pease LLP; Rex W. Miller, II

(57) ABSTRACT

Presently disclosed is a spinal implant. In an embodiment, a spinal implant includes a porous body configured to promote bone growth. The porous body may have an attachment portion that is configured to secure the spinal implant to a fixation system attached to one or more vertebra. The porous body may also include a fusion plate extending from the attachment portion and configured to contact transverse processes, lamina, or facet of adjacent vertebrae. Accordingly, when the attachment portion is secured to the fixation system, the fusion plate may be maintained in compression against the transverse processes, lamina, or facet.

21 Claims, 1 Drawing Sheet

Related U.S. Application Data continuation of application No. PCT/US2018/054349, filed on Oct. 4, 2018.

(60) Provisional application No. 62/569,138, filed on Oct. 6, 2017.

(51) Int. Cl.
*A61B 17/80* (2006.01)
*A61F 2/28* (2006.01)
*A61F 2/30* (2006.01)
*A61F 2/00* (2006.01)

(52) U.S. Cl.
CPC ........ *A61B 17/707* (2013.01); *A61B 17/7041* (2013.01); *A61B 17/7059* (2013.01); *A61B 17/7062* (2013.01); *A61B 17/7064* (2013.01); *A61B 17/8004* (2013.01); *A61F 2/28* (2013.01); *A61F 2/2846* (2013.01); *A61F 2/4405* (2013.01); *A61F 2002/0086* (2013.01); *A61F 2002/285* (2013.01); *A61F 2002/3093* (2013.01); *A61F 2002/30237* (2013.01); *A61F 2002/30622* (2013.01); *A61F 2002/30784* (2013.01); *A61F 2002/30841* (2013.01); *A61F 2310/00023* (2013.01)

(58) Field of Classification Search
CPC .............. A61B 17/7002; A61B 17/707; A61B 17/7041; A61B 17/7059; A61B 17/7062; A61B 17/7064; A61B 17/80; A61B 17/8004
See application file for complete search history.

(56) References Cited

U.S. PATENT DOCUMENTS

| | | |
|---|---|---|
| 9,662,226 B2 | 5/2017 | Wickham |
| 10,881,525 B2* | 1/2021 | Mullin ............... A61B 17/7062 |
| 2006/0241601 A1* | 10/2006 | Trautwein .......... A61B 17/7067 |
| | | 606/279 |
| 2008/0140127 A1 | 6/2008 | Vasta et al. |
| 2011/0319936 A1 | 12/2011 | Gordon et al. |
| 2012/0172987 A1 | 7/2012 | Phillips et al. |
| 2012/0303061 A1 | 11/2012 | Bhatnagar et al. |
| 2013/0178094 A1 | 7/2013 | Huang et al. |
| 2013/0178904 A1* | 7/2013 | Arcenio ................ A61F 2/4405 |
| | | 606/248 |
| 2014/0005723 A1 | 1/2014 | Shah et al. |
| 2017/0007306 A1 | 1/2017 | Werner |
| 2019/0029733 A1* | 1/2019 | Mickiewicz ....... A61B 17/7067 |

FOREIGN PATENT DOCUMENTS

| | | |
|---|---|---|
| JP | 11502437 A | 3/1999 |
| JP | 2008535583 A | 9/2008 |
| JP | 2009509588 A | 3/2009 |
| JP | 2017505701 A | 2/2017 |
| WO | 2017055929 A2 | 4/2017 |

OTHER PUBLICATIONS

International Search Report and Written Opinion of the International Searching Authority (Form PCT/ISA/220), International Application No. PCT/US18/54349, dated Dec. 21, 2018.

* cited by examiner

SPINAL IMPLANT

CROSS-REFERENCE TO RELATED APPLICATIONS

This application is a continuation of U.S. patent application Ser. No. 16/450,274 filed Jun. 24, 2019, which is a continuation of PCT Application No. PCT/US18/54349 filed Oct. 4, 2018, which claims priority to and the benefit of U.S. Provisional Application No. 62/569,138 filed Oct. 6, 2017, the disclosures of which are incorporated by reference herein in their entirety.

BACKGROUND OF THE INVENTION

The present disclosure relates to a spinal implant, and more particularly, to a posterolateral, laminar and facet fusion device.

Spinal fusion has been developed to immobilize joints as a treatment for various conditions and disorders. Prior interbody implants placed between vertebra have shown improved rates of fusion due to the implant being under compression. Attempts to achieve bone growth in posterolateral vertebra fusion has been less successful than interbody fusion.

Spinal fusions of the lumbar spine typically are located either between the vertebral bodies or in the posterior lateral space. Posterior lateral fusions have the advantage of taking a shorter amount of time, creating less blood loss, and avoiding nerve retraction. When the lamina are not removed, a laminar fusion may be applied. However, fusion rates are lower than interbody fusions. This is thought to be in part because Wolf's law (fusion under compressive forces) cannot be applied. Unless a solid fusion can be obtained, screw and rod fusion constructs will likely break because of metal fatigue. Fusions and screw/rod fracture happen over a variable length of time. Posterior lateral fusions require a source of bone. Traditionally, this can either involve local bone, iliac crest graft, and/or banked bone. Other materials can be applied such as demineralized bone matrix, and synthetic materials. There are variable fusion rates with different types of materials. It is recognized that interbody fusions have the highest fusion rates, followed by posterolateral fusions. This is thought to be because of the application of compressive force.

Recently porous titanium has been introduced into fusion devices. To date, it has been used in interbody devices to augment interbody fusions. However, it has not been applied to laminar or posterolateral fusion or facet fusions.

Accordingly, there remains a need for improved spinal implants for posterolateral, laminar and facet fusion that overcome the challenges of these prior solutions.

SUMMARY OF THE INVENTION

Presently disclosed is a spinal implant. In an embodiment, a spinal implant includes a porous body configured to promote bone growth, the body having an attachment portion configured to secure the spinal implant to a fixation system attached to one or more vertebra, and a fusion plate extending from the attachment portion, and offset from the attachment portion configured to contact transverse processes, lamina, or facet of adjacent vertebrae, such that when the attachment portion is secured to the fixation system, the fusion plate is maintained in compression against the transverse processes, lamina, or facet.

In some embodiments, the spinal implant comprises porous titanium. In some embodiments, the attachment portion includes a hook configured to extend at least partially around a rod between a pair of bone fasteners of the fixation system. In some embodiments, the attachment portion further includes apertures to receive a screw to secure the hook to a rod of the fixation system. In some embodiments, the attachment portion includes an aperture to receive a screw to secure the spinal implant to a bone fastener of the fixation system.

In some embodiments, the porous body further includes an extension portion between the attachment portion and the fusion plate, wherein the extension portion positions the fusion plate with respect to the attachment portion. In some embodiments, the extension portion is adjustable to position the fusion plate with respect to the attachment portion.

In some embodiments, the fusion plate has a concave upper surface configured to receive bone material. In some embodiments, the fusion plate has a convex lower surface configured to contact the transverse processes or the lamina of the adjacent vertebrae. In some embodiments, the fusion plate further has a plurality of protrusions on the convex lower surface configured to promote contact with the transverse processes or the lamina of the adjacent vertebrae.

Also disclosed is a spinal implant system. In some embodiments, the spinal implant system includes a pair of bone fasteners configured to be fixed to adjacent vertebrae; a rod extending between and secured by the pair of bone fasteners; and a spinal implant having a porous body configured to promote bone growth, the body having an attachment portion configured to extend at least partially around the rod between the pair of bone fasteners to secure the spinal implant to the rod, and a fusion plate extending from the attachment portion, and offset from the attachment portion configured to contact transverse processes or lamina of the adjacent vertebrae, such that when the attachment portion is secured to the rod, the fusion plate is maintained in compression against the transverse processes or lamina.

In some embodiments, the spinal implant includes an attachment portion configured to secure the spinal implant to a fixation system attached to one or more vertebra of a spine, and a fusion plate configured to promote contact with transverse processes or lamina of adjacent vertebrae, the fusion plate extending from the attachment portion and offset from the attachment portion, such that, when the attachment portion is secured to the fixation system, the fusion plate is maintained in compression against the transverse processes or lamina. In some of these embodiments, the spinal implant comprises a porous material selected to promote bone growth. In further embodiments, the porous material comprises porous titanium. In further embodiments, at least a portion of the spinal implant comprises a non-porous material. In some embodiments, the fusion plate includes a convex lower surface. In further embodiments, the fusion plate includes a plurality of protrusions on the convex lower surface. In even further embodiments, the plurality of protrusions are configured to promote contact with the transverse processes or the lamina of the adjacent vertebrae. In some embodiments, the fusion plate includes a concave upper surface configured to receive bone material. In further embodiments, the concave upper surface defines a trough. In some embodiments, the attachment portion includes a hook configured to extend at least partially around a rod of the fixation system. In some embodiments, the attachment portion includes a hook. In further embodiments, the fixation system includes a pair of bone fasteners attachable to adjacent vertebrae and a rod extending between the pair of bone fasteners. In other further embodiments, the hook is configured to extend at least partially around the rod between the pair of bone fasteners. In other further embodiments, the attachment portion includes apertures to receive a screw to secure the hook to the rod. In some embodiments, the attachment portion includes an aperture configured to receive a screw for securing the spinal implant to a bone fastener of the fixation system. In some embodiments, an extension portion between the attachment portion and the fusion plate, wherein the extension portion positions the fusion plate with respect to the attachment portion. In further embodiments, the extension portion extends laterally from the attachment portion a predetermined distance to align the fusion plate. In even further embodiments, the extension portion is adjustable to vary the predetermined distance position laterally extending between the fusion plate and the attachment portion. In further embodiments, the extension portion extends at an angle between the attachment portion and the fusion plate. In even further embodiments, the extension portion is adjustable to vary the angle between the attachment portion and the fusion plate.

Also disclosed herein is an implant system for fusing adjacent vertebrae. The implant system may include a means for securing adjacent vertebrae together and thereby inhibiting relative movement of the adjacent vertebrae. The implant system may also include a means for contacting transverse processes, lamina, or facet of the adjacent vertebrae and promoting bone grown to achieve fusion. The implant system may also include a means for attaching the contacting means to the securing means and thereby maintaining the contacting means in compression with the transverse processes, lamina, or facet to be fused.

BRIEF DESCRIPTION OF THE FIGURES

The invention can be understood from the following detailed description of exemplary embodiments of the invention taken in conjunction with the accompanying drawings.

DETAILED DESCRIPTION

This invention relates in general to a spinal implant system for posterolateral, laminar and facet fusion.

Figure 1:
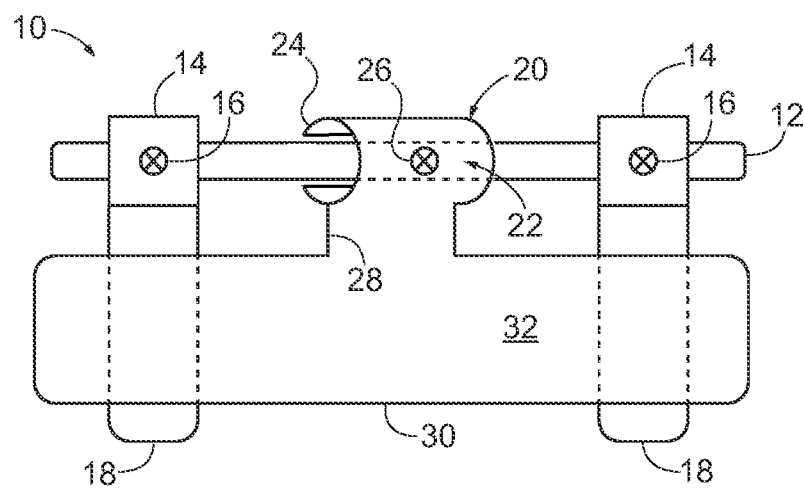
FIG. 1 is a top view of spinal implant system.
Figure 2:
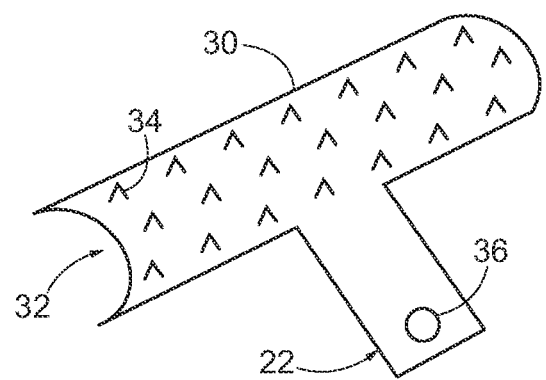
FIG. 2 is bottom view of another embodiment of a spinal implant.

Referring generally to FIGS. 1 and 2, a spinal implant system is disclosed. A spinal implant system 10 may include a fixation system. The fixation system may include one or more of a rod 12, and bone fasteners 14. As shown in FIG. 1, a pair of bone fasteners 14 are fastened to adjacent vertebra. A rod 12 extends between the pair of bone fasteners 14, and is secured in place by screws 16. The fixation system thereby inhibits movement of the adjacent vertebra.

The spinal implant system also includes a spinal implant having a body 20. The body 20 may be formed of a porous material selected to promote bone growth. In one embodiment, the body is formed of porous titanium with a modulus similar to nature bone. In other embodiments, selected portions of the body are formed of porous material while other portions are formed of non-porous materials. In some embodiments, the body of the spinal implant is formed by an additive manufacturing process, such as 3D printing. In some embodiments, the porous material forms a lattice having pores of approximately 0.75 millimeter in diameter.

The body 20 generally includes an attachment portion 22 and a fusion plate 30. In one embodiment, the attachment portion 20 is configured to secure the spinal implant to a rod 12 of the fixation system. As shown in FIG. 1, the attachment portion 22 includes a hook 24 that extends at least partially around the rod 12. The attachment portion 22 may also include a screw 26. In one embodiment, the screw 26 passes through the attachment portion 22 and into a portion of the hook 24 thereby affixing the spinal implant to the rod 12.

In another embodiment, as shown in FIG. 2, the attachment portion 22 includes an aperture 36. The aperture 36 is configured to receive a screw to secure the spinal implant to a bone fastener of the fixation system. In this manner, the spinal implant may be secured to various components of the fixation system to provide the desired alignment with the transverse processes to be fused.

Referring again to FIG. 1, the body 20 also includes a fusion plate 30. The fusion plate 30 extends from the attachment portion 22 and may be connected to the attachment portion 22 by an extension portion 28 as discussed further below. The fusion plate 30 is configured to contact the adjacent transverse processes 18 of the adjacent vertebrae to be fused. The fusion plate 30 may have a generally rectangular profile such that when installed the fusion plate extends longitudinally along the spine. In other embodiments, the fusion plate may have an oval or rounded profile as desired to accommodate the specific geometry of an individual patient's transverse processes. In yet other embodiments, the extension portion 28 may be formed of a deformable material such that the extension portion 28 may be adjusted to properly position the attachment portion 22 relative to the fusion plate 30 for a particular patient.

The fusion plate 30 may be further configured to improve contact with the transverse processes 18 and promote bone growth to achieve the desired fusion. The fusion plate 30 may also be configured to contact the lamina or facet. Referring to FIG. 2, in some embodiments the fusion plate 30 has a convex lower surface. A convex surface may generally conform to the contours of a patient's transverse processes. To further improve contact, the fusion plate 30 may include a plurality of protrusions 34 from the convex lower surface. In some embodiments, the protrusions 34 are localized raised portions of the lower surface that contact the transverse processes 18. The protrusions 34 may include repeating or random patterns of such raised portions. When the spinal implant is installed, the protrusions 34 contacting the transverse processes 18 apply increased pressure which is expected to further promote bone growth.

In some embodiments, the fusion plate 30 also includes a concave upper surface that forms a trough 32 as shown in FIG. 2. The trough 32 may be configured to receive bone material, such as bone chips, bone powder, or a slurry. The addition of bone materials may further promote the growth of new bone and accelerate the fusion of the transverse processes with the spinal implant.

In some embodiments, the spinal implant includes an extension portion 28 between the attachment portion 22 and the fusion plate 30. The extension portion 28 may be configured to facilitate placement of the spinal implant. In one embodiment, the extension portion 28 extends laterally from the attachment portion a predetermined distance such that the fusion plate is properly aligned with the transverse processes 18. In some embodiments, the extension portion 28 extends at an angle between the attachment portion 22 and the fusion plate 30. In such embodiments, the extension portion 28 positions the fusion plate on a different plane than the attachment portion so as to further position the fusion plate 30 in contact with the transverse processes. By positioning the fusion plate 30 on a different plane than the attachment portion 22, the spinal implant may be configured such that the fusion plate is further compressed against the transverse processes 18.

When the spinal implant is installed in a patient, the fusion plate 30 contacts the transverse processes 18 under pressure. By applying pressure at the points of contact, the spinal implant achieves compression that promotes bone growth in a manner not previously possible with prior art posterolateral vertebrae fusion devices. In this manner, the presently disclosed spinal implant may achieve an improved rate of fusion, which may be comparable to the rate of fusion presently available with interbody devices, but without the drawback and limitations inherent in such interbody devices.

A kit of spinal implants may also be provided that includes a selection of spinal implants of different sizes. A surgeon may select the spinal implant best suited to the particular size and geometry of the patient undergoing treatment. In addition, the spinal implants may be provided with extension portions having a variety of lengths and angles to accommodate variations in the configuration of the patients vertebrae and transverse processes. In this manner, the presently disclose spinal implant may be used in treatment of a wide variety of patients.

The presently disclosed spinal implant has been described primary in connection with fusions of the transverse processes, however, as will be understood the spinal implant may also provide for fusions of the lamina or facet.

The presently disclosed spinal implant system may provide numerous advantages for posterolateral, laminar and facet fusion. A spinal implant formed of porous titanium manufactured with an additive manufacturing process may allow bone growth into it and participate in the fusion. Such material is expected to fuse to the transverse processes and can be followed by eventual bony fusion of graft material. Compression can be applied to the spinal implant against the transverse processes. Local bone may be placed between the transverse processes and the spinal implant. This would put compression on either the spinal implant and the transverse process or the local bone. Graft material that is laid to bridge defects would also be placed under compression. The spinal implant would connect to and lock to the fixation system, such as the rod with a set screw. The spinal implant has a pore structure that allows bone growth. Local bone may be trapped under the spinal implant creating a compressed area that would further augment the fusion.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super elastic titanium alloys, cobalt-chrome alloys, stainless steel alloys, super elastic metallic alloys (e.g., Nitinol, super elasto-plastic metals, such as GUM METAL®. manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO.sub.4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tricalcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-(3), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

While principles and modes of operation have been explained and illustrated with regard to particular embodiments, it must be understood, however, that this may be practiced otherwise than as specifically explained and illustrated without departing from its spirit or scope.

What is claimed is:
1. A spinal implant comprising:
an attachment portion configured to secure the spinal implant to a fixation system attached to one or more vertebra of a spine; and
a fusion plate configured to fuse contact unilateral transverse processes, lamina, or facet of adjacent vertebrae longitudinally along the spine, the fusion plate extending from the attachment portion and offset from the attachment portion, such that, when the attachment portion is secured to the fixation system, the fusion plate is maintained in compression against the transverse processes, lamina, or facet to promote bone growth.

2. The spinal implant of claim 1, wherein the spinal implant comprises a porous material selected to promote bone growth.

3. The spinal implant of claim 2, wherein the porous material comprises porous titanium.

4. The spinal implant of claim 2, wherein at least a portion of the spinal implant comprises a non-porous material.

5. The spinal implant of claim 1, wherein the fusion plate includes a convex lower surface.

6. The spinal implant of claim 5, wherein the fusion plate includes a plurality of protrusions on the convex lower surface.

7. The spinal implant of claim 6, wherein the plurality of protrusions are configured to promote contact with the transverse processes, the lamina, or the facet of the adjacent vertebrae.

8. The spinal implant of claim 1, wherein the fusion plate includes a concave upper surface configured to receive bone material.

9. The spinal implant of claim 8, wherein the concave upper surface defines a trough.

10. The spinal implant of claim 1, wherein the attachment portion includes a hook configured to extend at least partially around a rod of the fixation system.

11. The spinal implant of claim 1, wherein the attachment portion includes a hook.

12. The spinal implant of claim 11, wherein the fixation system includes a pair of bone fasteners attachable to adjacent vertebrae and a rod extending between the pair of bone fasteners.

13. The spinal implant of claim 12, wherein the hook is configured to extend at least partially around the rod between the pair of bone fasteners.

14. The spinal implant of claim 12, wherein the attachment portion includes apertures to receive a screw to secure the hook to the rod.

15. The spinal implant of claim 1, further comprising an extension portion between the attachment portion and the fusion plate, wherein the extension portion positions the fusion plate with respect to the attachment portion.

16. The spinal implant of claim 15, wherein the extension portion extends laterally from the attachment portion a predetermined distance to align the fusion plate.

17. The spinal implant of claim 16, wherein the extension portion is adjustable to vary the predetermined distance position laterally extending between the fusion plate and the attachment portion.

18. The spinal implant of claim 15, wherein the extension portion extends at an angle between the attachment portion and the fusion plate.

19. The spinal implant of claim 18, wherein the extension portion is adjustable to vary the angle between the attachment portion and the fusion plate.

20. The spinal implant of claim 1, wherein the attachment portion includes an aperture configured to receive a screw for securing the spinal implant to a bone fastener of the fixation system.

21. An implant system for fusing adjacent vertebrae, the implant comprising:
   means for securing adjacent vertebrae together and thereby inhibiting relative movement of the adjacent vertebrae;
   means for contacting transverse processes, lamina, or facet of the adjacent vertebrae and promoting bone growth to achieve fusion between the transverse processes, lamina, or facet of the adjacent vertebrae; and
   means for attaching the contacting means to the securing means and thereby maintaining the contacting means in compression with the transverse processes, lamina, or facet to be fused.

* * * * *